(12) United States Patent
Melder (10) Patent No.: US 9,615,948 B2
(45) Date of Patent: Apr. 11, 2017

(54) DRUG ELUTING FOLDED STENT AND STENT DELIVERY SYSTEM

(75) Inventor: Robert Melder, Santa Rosa, CA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 1126 days.

(21) Appl. No.: 12/767,099

(22) Filed: Apr. 26, 2010

(65) Prior Publication Data
US 2011/0264187 A1 Oct. 27, 2011

(51) Int. Cl.
*A61F 2/84* (2006.01)
*A61F 2/91* (2013.01)
*A61F 2/958* (2013.01)

(52) U.S. Cl.
CPC ............... *A61F 2/91* (2013.01); *A61F 2/958* (2013.01); *A61F 2230/0054* (2013.01); *A61F 2250/0068* (2013.01); *Y10T 29/49982* (2015.01)

(58) Field of Classification Search
CPC ........................... A61F 2250/0068; A61F 2/91
USPC ....................................... 623/1.11, 1.12, 1.42
See application file for complete search history.

(56) References Cited

U.S. PATENT DOCUMENTS

| | | |
|---|---|---|
| 4,739,762 A | 4/1988 | Palmaz |
| 5,133,732 A | 7/1992 | Wiktor |
| 5,292,331 A | 3/1994 | Boneau |
| 5,421,955 A | 6/1995 | Lau |
| 5,605,696 A | 2/1997 | Eury et al. |
| 6,071,305 A | 6/2000 | Brown et al. |
| 6,090,127 A | 7/2000 | Globerman |
| 6,290,721 B1 | 9/2001 | Heath |
| 6,425,855 B2 | 7/2002 | Tomonto |
| 6,506,437 B1 * | 1/2003 | Harish ................. A61L 31/10 427/2.25 |
| 6,849,085 B2 | 2/2005 | Marton |
| 2004/0172124 A1 | 9/2004 | Vallana et al. |
| 2006/0122689 A1 * | 6/2006 | Kocur et al. ................. 623/1.15 |
| 2008/0181927 A1 * | 7/2008 | Zhao ............................. 424/423 |
| 2008/0208313 A1 | 8/2008 | Yu et al. |
| 2008/0300669 A1 * | 12/2008 | Hossainy ..................... 623/1.15 |
| 2008/0306579 A1 * | 12/2008 | Dolan et al. ................. 623/1.11 |
| 2011/0066227 A1 * | 3/2011 | Meyer et al. ................ 623/1.42 |

FOREIGN PATENT DOCUMENTS

| | | |
|---|---|---|
| EP | 1172074 | 1/2002 |
| WO | WO 2004/064911 | 8/2004 |
| WO | WO 2008/033711 | 3/2008 |
| WO | WO 2011/034733 | 3/2011 |

* cited by examiner

Primary Examiner — Katherine Rodjom (57) ABSTRACT

The drug eluting folded stent and a stent delivery system, which includes a stent having a plurality of struts interconnected to form a tubular body. At least one of the struts includes a U-shaped strut having in cross-section a first leg, a second leg, and a closed end connecting the first leg and the second leg, wherein the first leg, the second leg, and the closed end define a recess having a drug release opening opposite the closed end; and a drug coating disposed on the first leg, the second leg, and the closed end within the recess. The drug release opening is sized to release a drug from the drug coating at a predetermined drug elution rate.

27 Claims, 8 Drawing Sheets

DRUG ELUTING FOLDED STENT AND STENT DELIVERY SYSTEM

TECHNICAL FIELD

The technical field of this disclosure is medical implant devices, particularly, drug eluting folded stents and stent delivery systems.

BACKGROUND OF THE INVENTION

Stents are generally cylindrical shaped devices that are radially expandable to hold open a segment of a blood vessel or other anatomical lumen after implantation into the body lumen. Stents have been developed with coatings to deliver drugs or other therapeutic agents.

Stents are used in conjunction with balloon catheters in a variety of medical therapeutic applications including intravascular angioplasty. For example, a balloon catheter device is inflated during PTCA (percutaneous transluminal coronary angioplasty) to dilate a stenotic blood vessel. The stenosis may be the result of a lesion such as a plaque or thrombus. After inflation, the pressurized balloon exerts a compressive force on the lesion thereby increasing the inner diameter of the affected vessel. The increased interior vessel diameter facilitates improved blood flow. Soon after the procedure, however, a significant proportion of treated vessels re-narrow.

To prevent restenosis, short flexible cylinders, or stents, constructed of metal or various polymers are implanted within the vessel to maintain lumen size. The stents acts as a scaffold to support the lumen in an open position. Various configurations of stents include a cylindrical tube defined by a mesh, interconnected stents or like segments. Some exemplary stents are disclosed in U.S. Pat. No. 5,292,331 to Boneau, U.S. Pat. No. 6,090,127 to Globerman, U.S. Pat. No. 5,133,732 to Wiktor, U.S. Pat. No. 4,739,762 to Palmaz and U.S. Pat. No. 5,421,955 to Lau. Balloon-expandable stents are mounted on a collapsed balloon at a diameter smaller than when the stents are deployed. Stents can also be self-expanding, growing to a final diameter when deployed without mechanical assistance from a balloon or like device.

Drug eluting stents currently employ exterior coatings with or without polymers on metal struts to hold a drug for subsequent elution and delivery of the drug to surrounding tissue. Unfortunately, such coatings present a number of problems and limitations. The coatings are fragile and can fracture and fragment during manufacture, delivery, deployment, or use. Fracture during manufacture increases the cost and complexity of manufacture. Fracture during delivery, deployment, or use can reduce the effectiveness of the stent due to lost drug and can pose a risk to the patient if fragments block blood flow. The drug elutes from the coating surface, so the duration of drug elution is limited by the coating thickness, i.e., the mean diffusion length of the drug within the polymer coating. In addition, metal struts can fatigue and cracks can propagate through metal struts during use, fracturing the metal struts and creating fragments which can present a hazard to the patient. Concerns have also been raised over the long-term effects of polymers in contact with the body.

It would be desirable to have a drug eluting folded stent and stent delivery system that would overcome the above disadvantages.

SUMMARY OF THE INVENTION

One aspect of the invention provides a stent delivery system including a catheter; a balloon operably attached to the catheter; and a stent disposed on the balloon, the stent including a plurality of struts interconnected to form a tubular body. At least one of the struts includes a U-shaped strut having in cross-section a first leg, a second leg, and a closed end connecting the first leg and the second leg, wherein the first leg, the second leg, and the closed end define a recess having a drug release opening opposite the closed end; and a polymer drug coating disposed on the first leg, the second leg, and the closed end within the recess. The drug release opening is sized to release a drug from the drug coating at a predetermined drug elution rate.

Another aspect of the invention provides a stent including a plurality of struts interconnected to form a tubular body. At least one of the struts includes a U-shaped strut having in cross-section a first leg, a second leg, and a closed end connecting the first leg and the second leg, wherein the first leg, the second leg, and the closed end define a recess having a drug release opening opposite the closed end; and a drug coating disposed on the first leg, the second leg, and the closed end within the recess. The drug release opening is sized to release a drug from the drug coating at a predetermined drug elution rate.

Another aspect of the invention provides a method of manufacturing a stent including providing a rectangular metal ribbon having a first side and a second side; applying a drug coating to the first side of the rectangular metal ribbon to form a coated ribbon having a long axis; folding and laterally compressing the coated ribbon along the long axis to form a U-shaped wire, the U-shaped wire having a drug release opening sized to release a drug from the drug coating at a predetermined drug elution rate; and fashioning the U-shaped wire into the stent.

The foregoing and other features and advantages of the invention will become further apparent from the following detailed description of the presently preferred embodiments, read in conjunction with the accompanying drawings. The detailed description and drawings are merely illustrative of the invention, rather than limiting the scope of the invention being defined by the appended claims and equivalents thereof.

DETAILED DESCRIPTION

Figure 1:
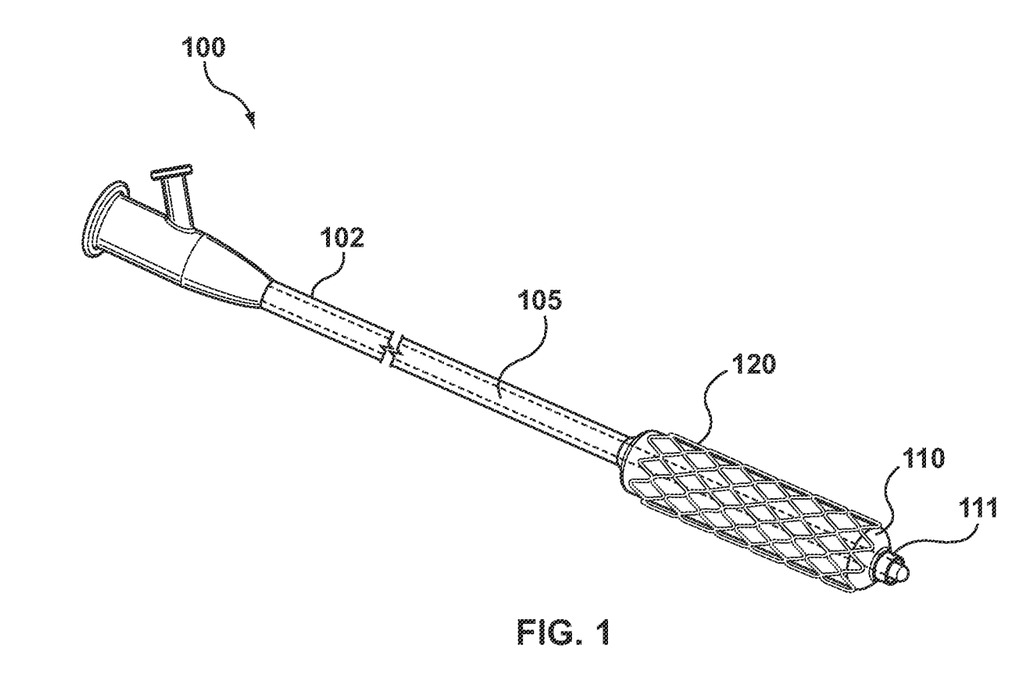
FIG. 1 is a perspective view of a stent delivery system made in accordance with the invention.

FIG. 1 is a perspective view of a stent delivery system made in accordance with the invention. The stent delivery system 100 includes a catheter 105, a balloon 110 operably attached to the catheter 105, and a stent 120 disposed on the balloon 110. The stent 120 is operable for use in a vessel having a vessel wall forming a vessel lumen. The stent 120 includes a number of struts interconnected to form a tubular body. At least one of the struts is a U-shaped strut with a recess and a drug coating disposed on the U-shaped strut within the recess. In one embodiment, all of the struts are U-shaped struts.

The balloon 110, shown in an inflated state, can be any variety of balloons capable of expanding the stent 120. The balloon 110 can be manufactured from a material such as polyethylene, polyethylene terephthalate (PET), nylon, Pebax® polyether-block co-polyamide polymers, or the like. In one embodiment, the stent delivery system 100 can include retention means 111, such as mechanical or adhesive structures, for retaining the stent 120 on the balloon 110 until the stent 120 is deployed. The catheter 105 may be any variety of balloon catheter, such as a PTCA (percutaneous transluminal coronary angioplasty) balloon catheter, capable of supporting a balloon during angioplasty. The stent delivery system 100 can also include a sheath 102 through which the stent 120 can be delivered to the deployment site.

Figure 2:
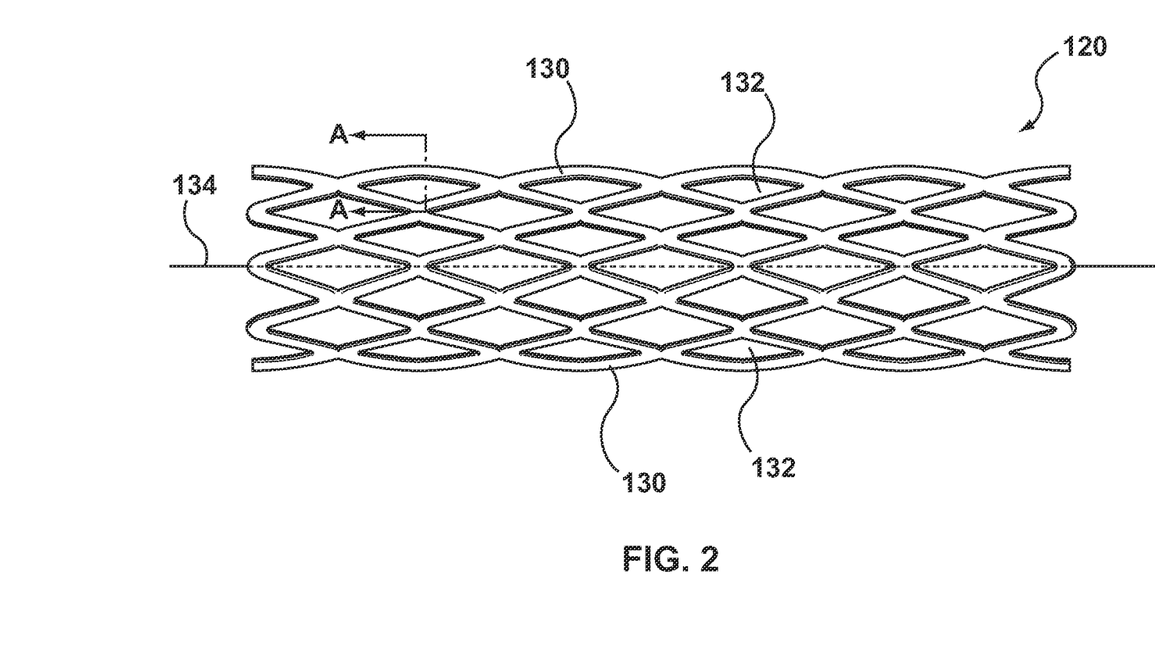
FIG. 2 is a side view of a drug eluting folded stent made in accordance with the invention.

FIG. 2 is a side view of a drug eluting folded stent made in accordance with the invention. The stent includes a number of struts interconnected to form a tubular body. At least one of the struts is a U-shaped strut having in cross-section a first leg, a second leg, and a closed end connecting the first leg and the second leg, wherein the first leg, the second leg, and the closed end define a recess having a drug release opening opposite the closed end; and a drug coating disposed on the first leg, the second leg, and the closed end within the recess. The drug release opening is sized to release a drug from the drug coating at a predetermined drug elution rate. The stent 120 can be installed in the stent delivery system of FIG. 1 for implantation in a body lumen, such as a vessel lumen.

Referring to FIG. 2, the stent 120 includes a number of struts 130 interconnected to form the tubular body of the stent 120. At least one of the struts 130 is a U-shaped strut 136 with a recess and a drug coating disposed on the U-shaped strut 136 within the recess. The stent 120 includes at least one opening 132 and has a central axis 134 with openings 132 generally perpendicular to the central axis. The pattern of the struts 130 can be W-shaped or can be a more complex shape with the elements of one segment continuing into the adjacent segment. In one embodiment, the stent 120 can be expanded by a balloon or another device. In another embodiment, the stent 120 can be self-expanding. In one embodiment, an outer drug coating (not shown) can be disposed on at least one of the struts.

Figure 3A:
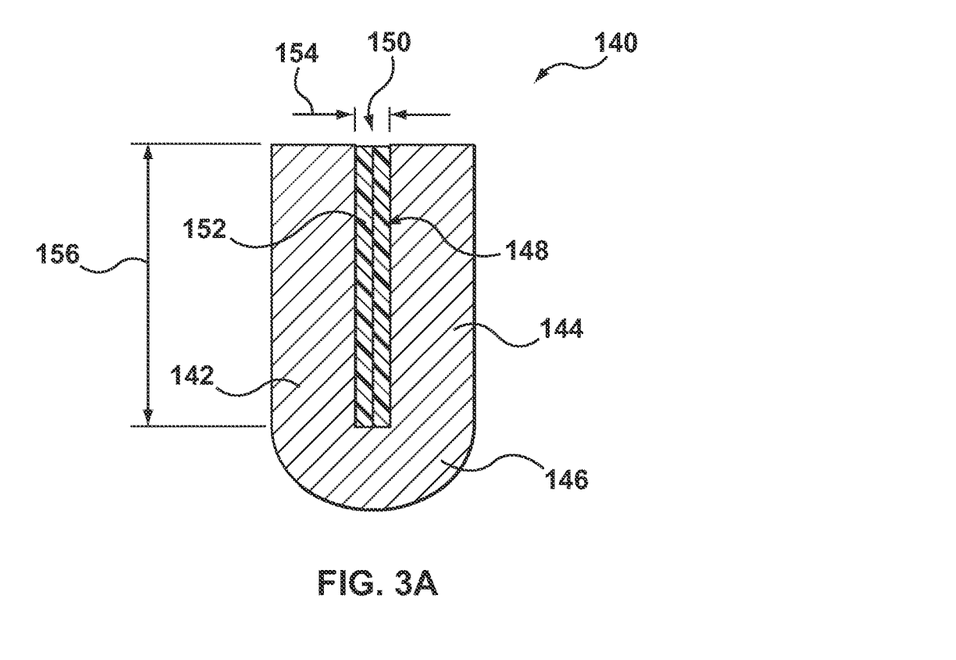
FIGS. 3A & 3B are cross section views of a strut of a drug eluting folded stent made in accordance with the invention.
Figure 3B:
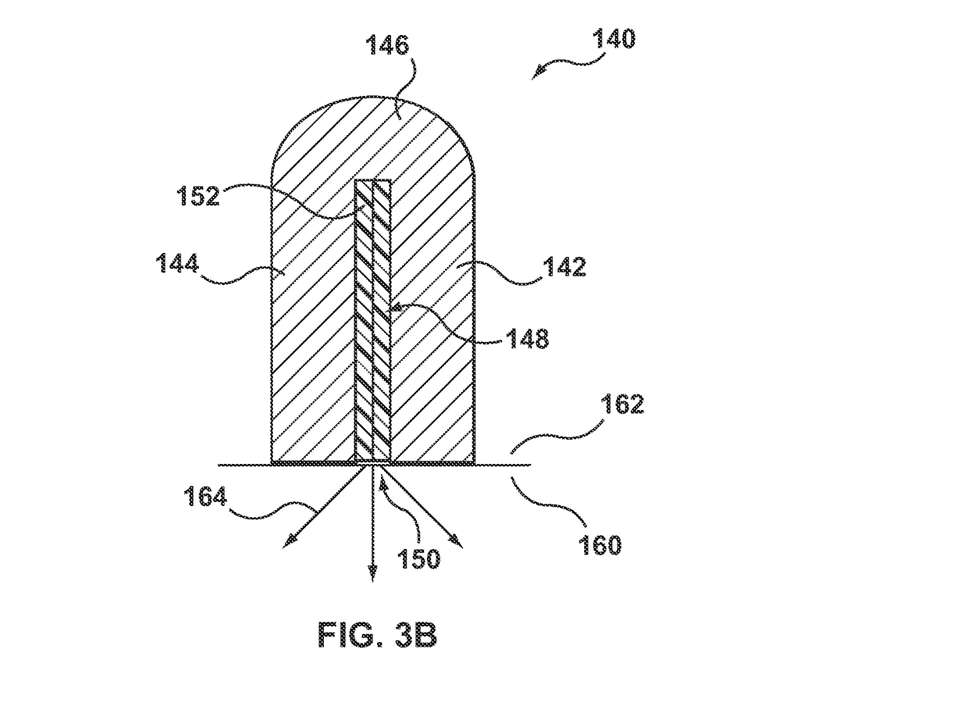

FIGS. 3A & 3B are cross section views of a strut of a drug eluting folded stent made in accordance with the invention. The strut is a U-shaped strut having in cross-section a first leg, a second leg, and a closed end connecting the first leg and the second leg, wherein the first leg, the second leg, and the closed end define a recess having a drug release opening opposite the closed end; and a drug coating disposed on the first leg, the second leg, and the closed end within the recess. The drug release opening is sized to release a drug from the drug coating at a predetermined drug elution rate. The cross section view is taken at Section A-A of FIG. 2.

Referring to FIG. 3A, which is a cross section view of a U-shaped strut, the U-shaped strut 140 includes a first leg 142, a second leg 144, and a closed end 146 connecting the first leg 142 and the second leg 144. The first leg 142, the second leg 144, and the closed end 146 are a unitary metal ribbon and define a recess 148 having a drug release opening 150 opposite the closed end 146. A drug coating 152 is disposed on the first leg 142, the second leg 144, and the closed end 146 and lies within the recess 148. The drug release opening 150 is sized to release a drug from the drug coating 152 at a predetermined drug elution rate. The drug coating 152 adheres to the first leg 142, the second leg 144, and the closed end 146. In one embodiment, the drug coating 152 adheres the first leg 142 to the second leg 144. In one embodiment, the drug coating 152 fills the recess 148.

The dimensions of the U-shaped strut 140 can be selected to provide desired mechanical characteristics, a predetermined drug elution rate, and a predetermined drug elution duration. The materials and thickness of the drug coating 152 and metal ribbon forming the U-shaped strut 140 can be selected to provide the desired stiffness and resiliency. In one embodiment, the drug release opening 150 has an opening width 154 equal to the total thickness of the drug coating 152 in the recess 148 (the thickness on the first leg 142 plus the thickness on the second leg 144) and selected to provide a predetermined drug elution rate. The thicker the drug coating 152, the greater the drug reservoir and surface area available for drug release, and consequently, the drug can be eluted from the drug coating 152 more quickly and for a longer duration. In another embodiment, the U-shaped strut 140 has a recess length 156 sized to release the drug from the drug coating 152 for a predetermined drug elution duration. The greater the recess length 156 of the U-shaped strut 140, the greater the available drug reservoir and the further the drug diffuses through the drug coating 152 before exiting the drug release opening 150, extending the drug elution duration. In one example, the U-shaped strut 140 has a recess length 156 of 90 µm and an opening width 154 of 5 µm, with the metal ribbon having a thickness of 25 µm. In another example extending elution duration, the U-shaped strut 140 has a recess length 156 of 150 µm and an opening width 154 of 10 µm. In yet another example decreasing radial strength and decreasing the rate and amount of delivered drug, the U-shaped strut 140 has a recess length 156 of 45 µm and an opening width 154 of 10 µm, with the metal ribbon having a thickness of 25 µm.

FIG. 3B, in which like elements share like reference numbers with FIG. 3A, is a cross section view of a U-shaped strut deployed in a vessel. The vessel has a vessel wall 160 and a vessel lumen 162. In this example, the drug release opening 150 is located on the outer diameter of the stent, so that the drug release opening 150 is in contact with the vessel wall 160. The drug diffusing from the drug coating 152 and through the drug release opening 150 enters the vessel wall 160 as indicated by the arrows 164. Those skilled in the art will appreciate that, in another example (not shown), the drug release opening can be located on the inner diameter of the stent, so that the drug release opening is in communication with and delivers the drug into the vessel lumen.

Figure 4A:
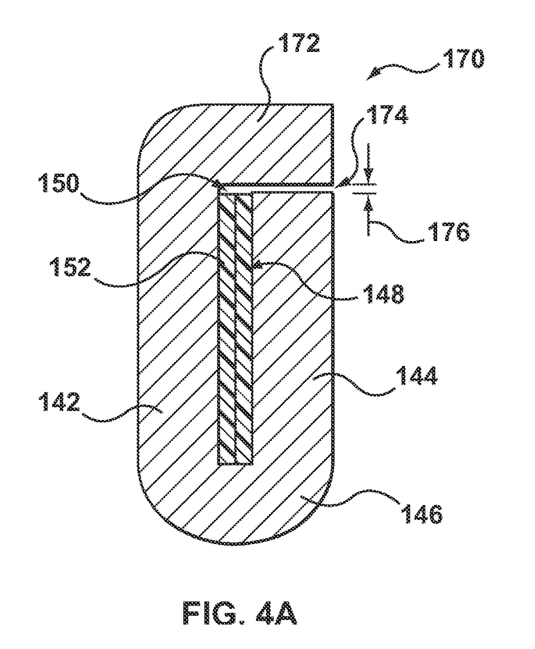
FIGS. 4A & 4B are cross section views of another embodiment of a strut of a drug eluting folded stent made in accordance with the invention.
Figure 4B:
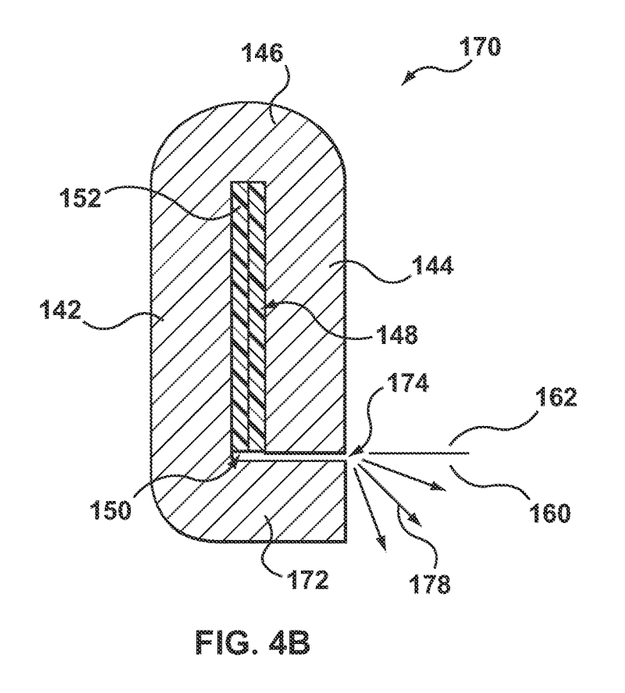

FIGS. 4A & 4B, in which like elements share like reference numbers with FIG. 3A, are cross section views of another embodiment of a strut of a drug eluting folded stent made in accordance with the invention. In this embodiment, the U-shaped strut includes a cap end defining a delivery port.

Referring to FIG. 4A, which is a cross section view of a U-shaped strut, the U-shaped strut 170 includes a cap end 172 attached to the first leg 142 and disposed over the drug release opening 150. The cap end 172 and the second leg 144 define a delivery port 174 in communication with the drug release opening 150. The delivery port 174 is sized with a port width 176 to release the drug from the drug coating 152 at a predetermined drug elution rate less than or equal to the predetermined drug elution rate which would occur when the cap end 172 is not present and the predetermined drug elution rate is set by the opening width 154 of the drug release opening 150 alone. The narrower the delivery port 174, the slower drug diffusion occurs from the drug coating 152, reducing the drug elution rate and extending the drug elution duration. In one example, the U-shaped strut 170 has a port width 176 of 5 µm. In another example extending elution duration, the U-shaped strut 170 has a port width 176 of 2 µm.

The cap end 172 can be uncoated or can be coated to include the drug coating 152 in the recess 148 and delivery port 174. When the cap end 172 is uncoated, the delivery port 174 acts as a plenum to limit diffusion of drug from the drug coating 152. When the cap end 172 includes the drug coating 152 in the recess 148 and delivery port 174, the drug coating 152 within the recess 148 further limits the diffusion of drug from the drug coating 152.

FIG. 4B, in which like elements share like reference numbers with FIG. 4A, is a cross section view of a U-shaped strut deployed in a vessel. The U-shaped strut 170 has the delivery port 174 open to a side of the U-shaped strut 170 adjacent the second leg 144. In this example, the delivery port 174 is located toward the outer diameter of the stent, so that the delivery port 174 is in or near the vessel wall 160. The drug diffusing from the drug coating 152, through the drug release opening 150, and through the delivery port 174 enters the vessel wall 160 as indicated by the arrows 178. Those skilled in the art will appreciate that, in another example (not shown), the delivery port can be located toward the inner diameter of the stent, so that the delivery port is in communication with and delivers the drug into the vessel lumen 162.

Figure 5:
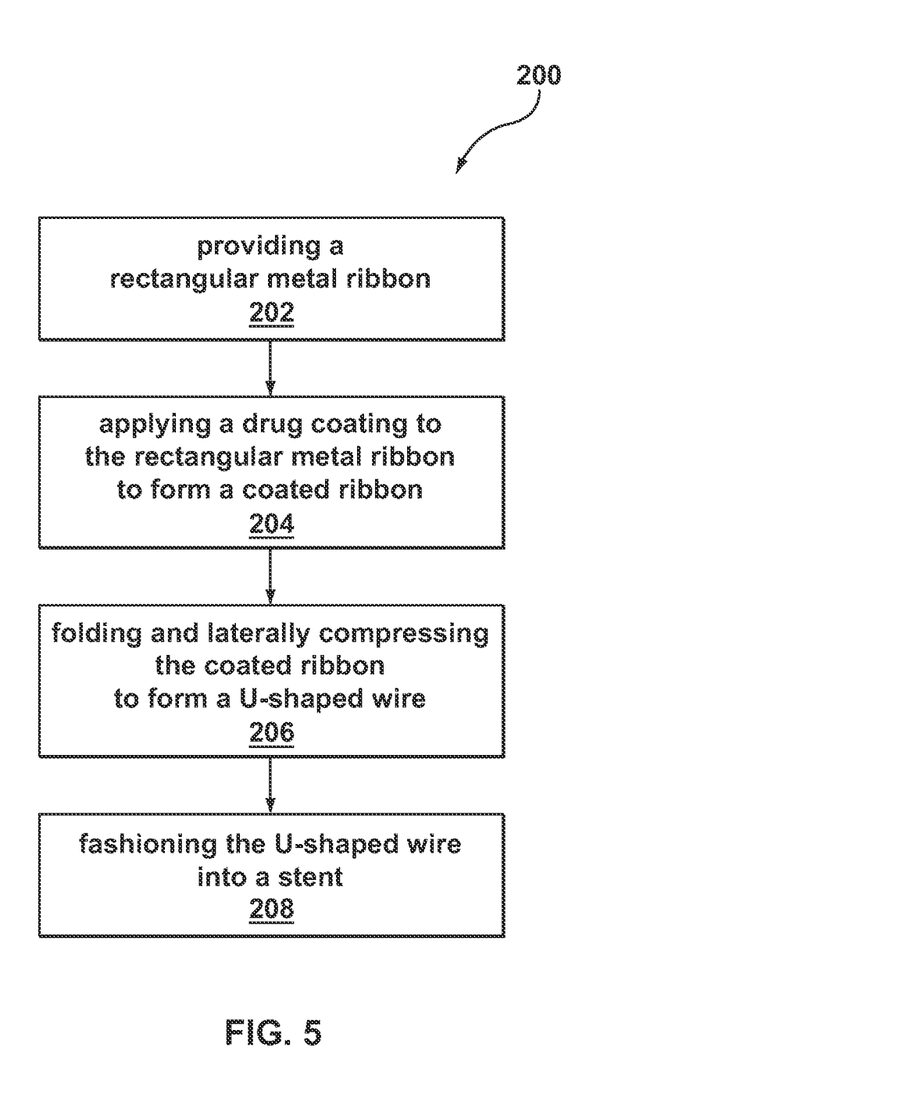
FIG. 5 is a flow chart of a method of manufacture of a drug eluting folded stent in accordance with the invention

FIG. 5 is a flow chart of a method of manufacture of a drug eluting folded stent in accordance with the invention. The method 200 includes providing a rectangular metal ribbon having a first side and a second side 202; applying a drug coating to the first side of the rectangular metal ribbon to form a coated ribbon having a long axis 204; folding and laterally compressing the coated ribbon along the long axis to form a U-shaped wire 206, the U-shaped wire having a drug release opening sized to release a drug from the drug coating at a predetermined drug elution rate; and fashioning the U-shaped wire into the stent 208.

The providing a rectangular metal ribbon having a first side and a second side 202 can include providing a polished and finished rectangular metal ribbon, which reduces the need to polish and finish the stent when fashioning the U-shaped wire into the stent.

The applying a drug coating to the first side of the rectangular metal ribbon to form a coated ribbon having a long axis 204 can include spraying the drug coating on the first side of the rectangular metal ribbon to form the coated ribbon. The spray can include a polymer, drug, and solvent. Those skilled in the art will appreciate that the applying can be performed by spraying, painting, rolling, electrostatic deposition, ink jet coating, spin coating, or the like as desired for a particular application. In one embodiment, the drug coating covers the whole first side of the rectangular metal ribbon. In another embodiment, the drug coating covers a portion of the first side of the rectangular metal ribbon, and another portion is left uncoated. In one embodiment, the uncoated portion can be used to form a cap end.

The folding and laterally compressing the coated ribbon along the long axis to form a U-shaped wire 206 forms the first leg, closed end, and second leg, and folds the drug coatings on the first leg and the second leg toward each other and together. The folding and laterally compressing also defines the recess and the drug release opening opposite the closed end. The drug release opening in the U-shaped wire is sized to release a drug from the drug coating at a predetermined drug elution rate. In one embodiment, the drug coating can be solidified before the folding and laterally compressing. In another embodiment, the drug coating can be maintained in an adhesive state before the folding and laterally compressing, and the drug coating solidified after the folding and laterally compressing to adhere the first leg and the second leg. Maintaining the drug coating in an adhesive state keeps the drug coating flexible so that the drug coating can fill the area between the first leg and the second leg of the coated ribbon and stick to both the first leg and the second leg of the coated ribbon. In one embodiment, the drug coating stays in an adhesive state as volatile compounds evaporate. In another embodiment, the drug coating can be maintained in an adhesive state by heating the drug coating. The drug coating can be solidified by curing, drying, and/or cooling the coated ribbon.

The fashioning the U-shaped wire into the stent 208 includes interconnecting the U-shaped wire to form the stent. The U-shaped wire can be interconnected by brazing, soldering, welding, weaving, or any other method of joining the U-shaped wire. In one embodiment, the whole stent is formed of the U-shaped wire. In another embodiment, part of the stent is formed of the U-shaped wire and another part of the stent is formed of different stock, such as solid wire, laser cut metal sheeting, or the like. When the method 200 starts with a polished and finished rectangular metal ribbon, little polishing and/or finishing of the stent is required. The finished stent can then be crimped to a balloon operably attached to a catheter when the stent is a balloon expandable stent.

The method 200 can further be used to form U-shaped wire with a cap end and a delivery port. The folding and laterally compressing 206 includes folding and laterally compressing the coated ribbon asymmetrically along the long axis to form a U-shaped wire with a first leg, a closed end, a second leg, and a cap end. The cap end and the second leg define a delivery port in communication with the drug release opening opposite the closed end. The delivery port is sized to release the drug from the drug coating at a predetermined drug elution rate less than or equal to the predetermined drug elution rate which would occur when the cap end is not present and the predetermined drug elution rate is set by the drug release opening alone. In one embodiment, the applying a drug coating to the first side of the rectangular metal ribbon to form a coated ribbon having a long axis 204 includes applying the drug coating to part of the first side of the rectangular metal ribbon so a portion of the coated ribbon forming the cap end is uncoated. The uncoated portion can be used to form an uncoated delivery port.

Those skilled in the art will appreciate that other approaches can be used to load the drug into the recess of the U-shaped strut. In one embodiment, the ribbon can be folded into the U-shape and the recess can be filled by capillary action through external application of a drug or drug-polymer mixture, followed by solidification of the applied material. In another embodiment, the U-shaped wire may be formed into the stent prior to the application of a drug or drug-polymer mixture, and the recess in the stent struts filled by external application of the drug or drug-polymer mixture and capillary filling of the recess, followed by solidification of the applied material.

Figure 6A:
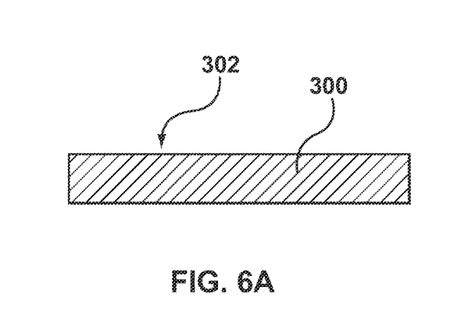
FIGS. 6A-6D are various views of a method of manufacture of a drug eluting folded stent in accordance with the invention.

FIGS. 6A-6D, in which like elements share like reference numbers, are various views of a method of manufacture of a drug eluting folded stent in accordance with the invention. FIG. 6A is a cross section view of a rectangular metal ribbon for use in a method of manufacture of a drug eluting folded stent in accordance with the invention. The rectangular metal ribbon 300 has a first side 302 to receive the drug coating. The rectangular metal ribbon 300 can be of any length perpendicular the cross section as desired for a particular application, with a long axis (not shown) along the length.

The materials of the rectangular metal ribbon 300 can be any biocompatible materials appropriate to the particular application. The rectangular metal ribbon 300 can be any biocompatible metal, such as stainless steel, cobalt alloy, cobalt chromium alloy, magnesium, or the like. The dimensions of the rectangular metal ribbon 300 can be selected as desired for a particular application. The thickness of the metal foil forming the rectangular metal ribbon 300 can be selected to provide the desired stiffness and mechanical characteristics for the stent. In one example, the thickness of the rectangular metal ribbon 300 can be between 10 and 30 µm. The rectangular metal ribbon 300 can be polished and finished before application of the drug coating to reduce the finishing work after fashioning the stent.

Figure 6B:
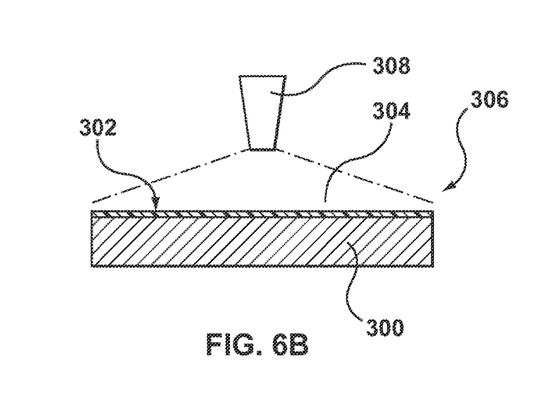

FIG. 6B is a cross section view of a rectangular metal ribbon with drug coating for use in a method of manufacture of a drug eluting folded stent in accordance with the invention. The rectangular metal ribbon 300 and the drug coating 304 form a coated ribbon 306. In one embodiment, the drug coating 304 is applied as a mixture of a polymer, drug, and solvent, with the mixture being applied to the first side 302 of the rectangular metal ribbon 300 with a sprayer 308.

The drug coating 304 can include a polymer and a drug, or a drug alone. Exemplary polymers include any polymer compatible with a selected drug or therapeutic agent, i.e., polymers such as BioLinx® polymer, poly(vinyl alcohol), poly(ethylene-vinyl acetate), polyurethane, polycaprolactone, polyglycolide, poly(lactide-co-glycolide), poly(ethylene oxide), poly(vinyl pyrrolidone), silicone, an acrylic polymer, an acrylic and acrylonitrile copolymer, a latex polymer, a thermoplastic polymer, a thermoset polymer, a biostable polymer, a biodegradable polymer, a blended polymer, a copolymer, combinations thereof, and the like.

Those skilled in the art will appreciate that any compatible combinations of polymer and drug can be used as desired for a particular application. Drug, as defined herein, includes any drug, therapeutic agent, bioactive agent, or the like intended to affect the structure or any function of the body of man or other animals.

Exemplary drugs include any drug, therapeutic agent, or bioactive agent that can diffuse through a selected polymer, such as an antirestenotic drug (e.g., rapamycin, rapamycin analogue, or rapamycin derivative to prevent or reduce the recurrence or narrowing and blockage of the bodily vessel), an anti-cancer drug (e.g., camptothecin or other topoisomerase inhibitors), an antisense agent, an antineoplastic agent, an antiproliferative agent, an antithrombogenic agent, an anticoagulant, an antiplatelet agent, an antibiotic, an anti-inflammatory agent, a steroid, a gene therapy agent, an organic drug, a pharmaceutical compound, a recombinant DNA product, a recombinant RNA product, a collagen, a collagenic derivative, a protein, a protein analog, a saccharide, a saccharide derivative, a bioactive agent, a pharmaceutical drug, a therapeutic substance, a combination thereof, and the like. Those skilled in the art will appreciate that in another embodiment that the drug can be omitted from the drug coating 304, so that the drug coating 304 is polymer alone without a drug.

Figure 6C:
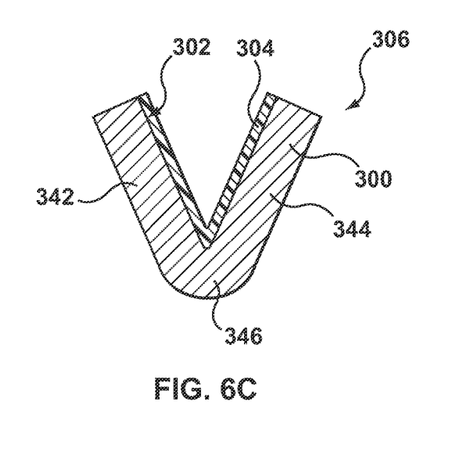

FIG. 6C is a cross section view of a partially folded coated ribbon for use in a method of manufacture of a drug eluting folded stent in accordance with the invention. The coated ribbon 306 is folded and laterally compressed along the long axis, forming a first leg 342, a closed end 346, and a second leg 344. In one embodiment, the drug coating 304 is solidified before the folding and laterally compressing. In another embodiment, the drug coating 304 is maintained in an adhesive state before the folding and laterally compressing, and the drug coating 304 is solidified after the folding and laterally compressing to adhere the first leg 342 and the second leg 344.

Figure 6D:
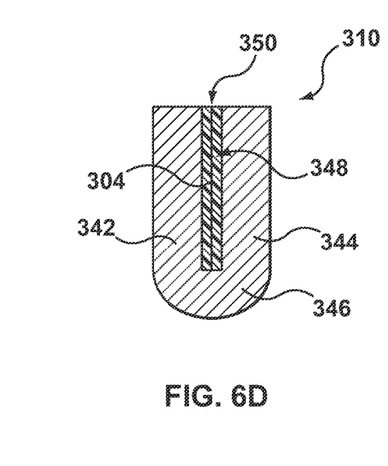

FIG. 6D is a cross section view of a U-shaped wire for use in a method of manufacture of a drug eluting folded stent in accordance with the invention. The U-shaped wire 310 includes the first leg 342, the second leg 344, and the closed end 346, which define a recess 348 having a drug release opening 350 opposite the closed end 346. The drug release opening 350 is sized to release a drug from the drug coating 304 at a predetermined drug elution rate. The U-shaped wire 310 can be fashioned into a stent with the drug release opening 350 oriented outward on the outer diameter of the stent, inward on the inner diameter of the stent, or any orientation between outward and inward.

FIGS. 7A-7E, in which like elements share like reference numbers with each other and with FIGS. 6A-6D, are various views of a method of manufacture of another drug eluting folded stent in accordance with the invention. In this embodiment, the U-shaped strut includes a cap end defining a delivery port.

Figure 7A:
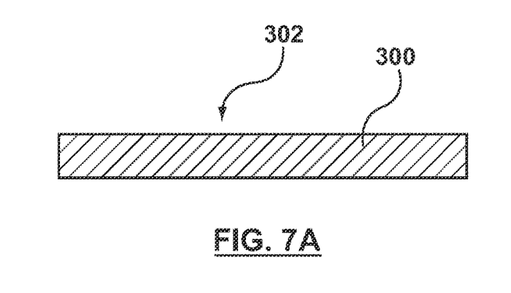
FIGS. 7A-7E are various views of a method of manufacture of another drug eluting folded stent in accordance with the invention.

FIG. 7A is a cross section view of a rectangular metal ribbon for use in a method of manufacture of a drug eluting folded stent in accordance with the invention. The rectangular metal ribbon 300 has a first side 302 to receive the drug coating. The rectangular metal ribbon 300 can be of any length perpendicular the cross section as desired for a particular application, with a long axis (not shown) along the length.

Figure 7B:
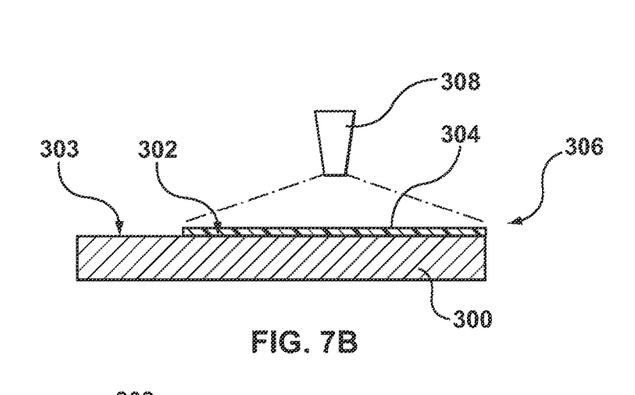

FIG. 7B is a cross section view of a rectangular metal ribbon with drug coating for use in a method of manufacture of a drug eluting folded stent in accordance with the invention. The rectangular metal ribbon 300 and the drug coating 304 form a coated ribbon 306. In one embodiment, the drug coating 304 is applied as a mixture of a polymer, drug, and solvent, with the mixture being applied to the first side 302 of the rectangular metal ribbon 300 with a sprayer 308. In this embodiment, the drug coating 304 covers a portion of the first side 302 of the rectangular metal ribbon 300 without covering the uncoated portion 303 of the first side 302.

Figure 7C:
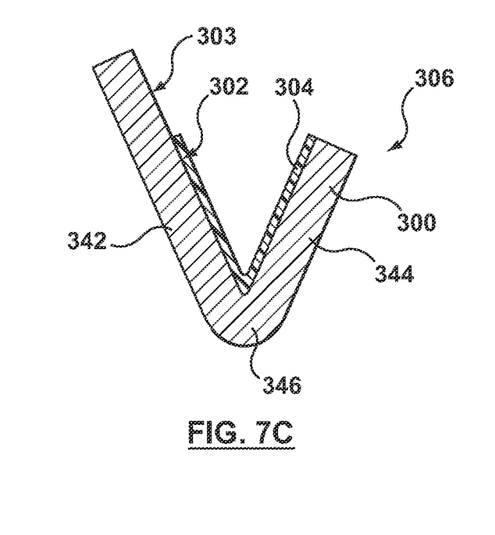

FIG. 7C is a cross section view of a partially folded coated ribbon for use in a method of manufacture of a drug eluting folded stent in accordance with the invention. The coated ribbon 306 is folded and laterally compressed asymmetrically along the long axis, forming a first leg 342, a closed end 346, and a second leg 344. The uncoated portion 303 of the first side 302 extends beyond the length of the second leg 344. In one embodiment, the drug coating 304 is solidified before the folding and laterally compressing. In another embodiment, the drug coating 304 is maintained in an adhesive state before the folding and laterally compressing, and the drug coating 304 is solidified after the folding and laterally compressing to adhere the first leg 342 and the second leg 344.

Figure 7D:
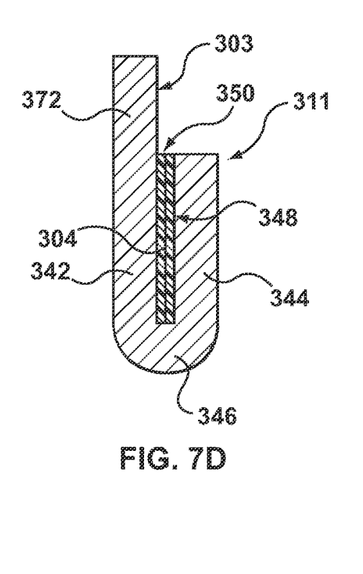
Figure 7E:
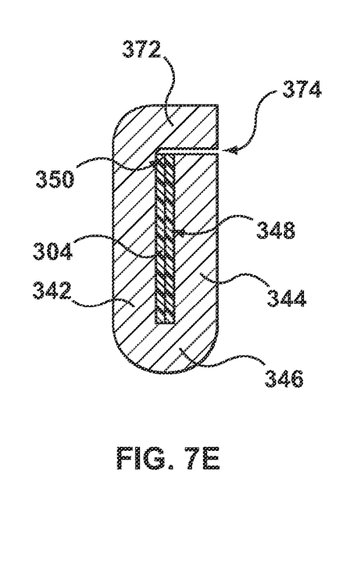

FIG. 7D is a cross section view of a laterally compressed coated ribbon for use in a method of manufacture of a drug eluting folded stent in accordance with the invention. The laterally compressed coated ribbon 311 includes the first leg 342, the second leg 344, and the closed end 346, which define a recess 348 having a drug release opening 350 opposite the closed end 346. The laterally compressed coated ribbon 311 also includes a cap end 372 along the length of the uncoated portion 303.

FIG. 7D is a cross section view of a U-shaped wire for use in a method of manufacture of a drug eluting folded stent in accordance with the invention. The cap end 372 of the U-shaped wire 330 is disposed over the drug release opening 350, so that the cap end 372 and the second leg 344 define a delivery port 374 in communication with the drug release opening 350. The delivery port 374 is sized with a port width 376 to release the drug from the drug coating 352 at a predetermined drug elution rate less than or equal to the predetermined drug elution rate which would occur when the cap end 372 is not present and the predetermined drug elution rate is set by the opening width 354 of the drug release opening 350 alone. The U-shaped wire 330 can be fashioned into a stent with the delivery port 374 oriented in any direction on the stent as desired for a particular application.

Figure 8A:
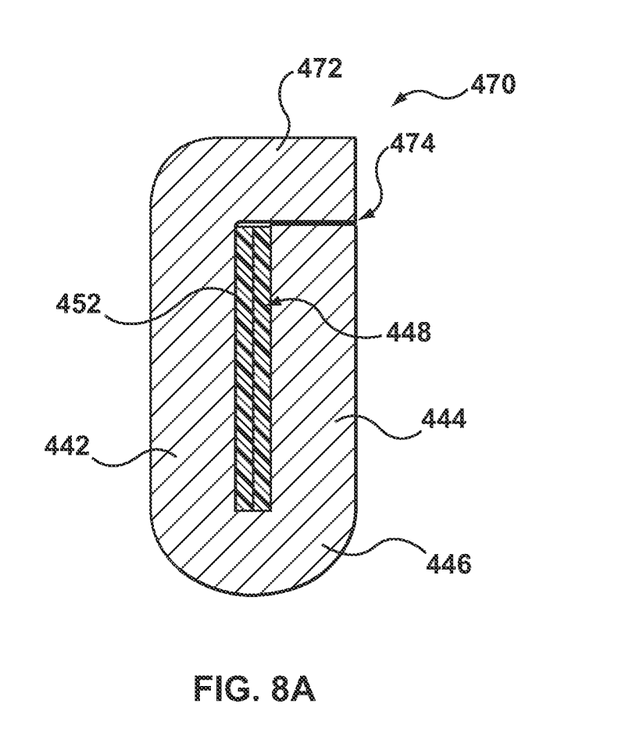
FIGS. 8A & 8B are cross section and top views, respectively, of another embodiment of a strut of a drug eluting folded stent made in accordance with the invention.
Figure 8B:
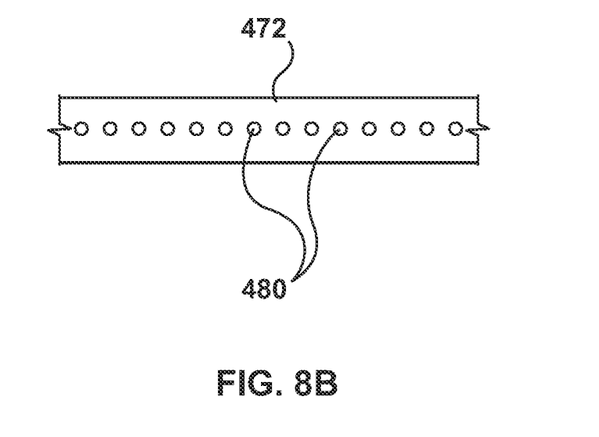

FIGS. 8A & 8B, in which like elements share like reference numbers, are cross section and top views, respectively, of another embodiment of a strut of a drug eluting folded stent made in accordance with the invention. In this embodiment, the folded stent is similar to the folded stent as illustrated in FIG. 4A and as manufactured in FIGS. 7A-7E, except the cap end is disposed against the second leg so there is no delivery port between the cap end and the second leg. The drug coating is sealed within the recess, so holes can be provided through one or more walls of the U-shaped strut to allow drug elution.

Referring to FIG. 8A, which is a cross section view of a U-shaped strut, the U-shaped strut 470 includes a cap end 472 attached to the first leg 442. The cap end 472 and the second leg 444 meet at an interface 474 to close off the recess 448 holding the drug coating 452. The cap end 472 can be uncoated or can be coated to the point where the first leg 442 meets the second leg 444 in the recess 448.

Referring to FIG. 8B, which is a detailed top view along a long axis of a U-shaped strut, the cap end 472 defines a number of drug delivery openings 480. The drug delivery openings 480 can be defined through the cap end 472, first leg 442, second leg 444, and/or the closed end 446 so the drug can elute from the U-shaped strut. The drug delivery openings 480 can be formed before or after the folding of the ribbon into the U-shape. Those skilled in the art will appreciate that the size, pattern, and location of the drug delivery openings can be selected as desired for a particular application.

It is important to note that FIGS. 1-8 illustrate specific applications and embodiments of the invention, and are not intended to limit the scope of the present disclosure or claims to that which is presented therein. For example, the U-shaped wire can be fashioned into devices other than stents. The U-shaped wire can be fashioned into drug eluting, electrically conducting components, such as electrodes, electrical conductors, pacing leads, or the like, by using electrically conducting alloys in the U-shaped wire. In other applications, the U-shaped wire can be incorporated into bone grafts to provide structural support and provide local delivery of growth factors to accelerate healing or into stent grafts or heart valve frames to provide accelerated engraftment of the devices. Upon reading the specification and reviewing the drawings hereof, it will become immediately obvious to those skilled in the art that myriad other embodiments of the invention are possible, and that such embodiments are contemplated and fall within the scope of the presently claimed invention.

While the embodiments of the invention disclosed herein are presently considered to be preferred, various changes and modifications can be made without departing from the spirit and scope of the invention. The scope of the invention is indicated in the appended claims, and all changes that come within the meaning and range of equivalents are intended to be embraced therein.

The invention claimed is:

1. A stent delivery system comprising:
a catheter;
a balloon operably attached to the catheter; and
a stent disposed on the balloon, the stent comprising a plurality of struts interconnected to form a tubular body, at least one of the struts comprising:
a U-shaped strut having in cross-section a first leg, a second leg, and a closed end connecting the first leg and the second leg, the first leg is longer than the second leg in cross-section, wherein the first leg, the second leg, and the closed end define a recess having a drug release opening opposite the closed end, the recess is sized to release a drug from a drug coated at a first predetermined drug elution rate, and wherein the first leg, the second leg, and the closed end define a first fold therebetween, the first fold extending along a long axis of the U-shaped strut in a unitary metal ribbon, the first leg having a second fold angled at about 90 degrees with respect to the first leg to form a cap end at a distal end thereof, the cap end is disposed over the recess and the second leg to enclose a drug coating within the recess, the cap end and the second leg defining a delivery port in communication with the drug release opening, the delivery port being sized to release the drug from the drug coating at a second predetermined drug elution rate less than or equal to the first predetermined drug elution rate, and wherein the cap end comprises a portion of the unitary metal ribbon forming the first leg.

2. The system of claim 1 wherein the stent has an outer diameter and an inner diameter, the drug release opening being located on the outer diameter.

3. The system of claim 1 wherein the stent has an outer diameter and an inner diameter, the drug release opening being located on the inner diameter.

4. The system of claim 1 wherein the drug coating adheres to the first leg, the second leg, and the closed end.

5. The system of claim 1 wherein the drug coating fills the recess.

6. The system of claim 1 wherein the drug coating comprises a polymer and a drug.

7. The system of claim 1 wherein the delivery port opens to a side of the U-shaped strut adjacent the second leg.

8. The system of claim 1 wherein the drug coating is further disposed on the cap end within the recess and the delivery port.

9. The system of claim 1 wherein the cap end is uncoated.

10. The system of claim 1 further comprising an outer drug coating disposed on at least one of the struts.

11. The system of claim 1 wherein a first leg width of the first leg is substantially equal to a second leg width of the second leg, wherein the first leg width and the second leg width are measured from the closed end to the drug release opening.

12. The system of claim 1 wherein the first leg comprises a substantially flat first leg surface from the first fold to the drug release opening, wherein the second leg comprises a substantially flat second leg surface from the first fold to the drug release opening, and wherein the substantially flat first leg surface faces the substantially flat second leg surface from the first fold to the drug release opening across the recess.

13. The system of claim 12 wherein the recess located between the substantially flat first leg surface and the substantially flat second leg surface comprises a substantially uniform recess width between the substantially flat first leg surface and the substantially flat second leg surface from the first fold to the drug release opening.

14. A stent comprising a plurality of struts interconnected to form a tubular body, at least one of the struts comprising:
a U-shaped strut having in cross-section a first leg, a second leg, and a closed end connecting the first leg and the second leg, the first leg is longer than the second leg in cross-section, wherein the first leg, the second leg, and the closed end define a recess having a drug release opening opposite the closed end, the recess is sized to release a drug from a drug coating at a first predetermined drug elution rate, and wherein the first leg, the second leg, and the closed end define a first fold therebetween, the first fold extending along a long axis of the U-shaped strut in a unitary metal ribbon, the first leg having a second fold angled at about 90 degrees with respect to the first leg to form a cap end at a distal end thereof, the cap end is disposed over the recess and the second leg to enclose a drug coating within the recess, the cap end and the second leg defining a delivery port in communication with the drug release opening, the delivery port being sized to release the drug from the drug coating at a second predetermined drug elution rate less than or equal to the first predetermined drug elution rate, and wherein the cap end comprises a portion of the unitary metal ribbon forming the first leg.

15. The stent of claim 14 wherein the stent has an outer diameter and an inner diameter, the drug release opening being located on the outer diameter.

16. The stent of claim 14 wherein the stent has an outer diameter and an inner diameter, the drug release opening being located on the inner diameter.

17. The stent of claim 14 wherein the drug coating adheres to the first leg, the second leg, and the closed end.

18. The stent of claim 14 wherein the drug coating fills the recess.

19. The stent of claim 14 wherein the drug coating comprises a polymer and a drug.

20. The stent of claim 14 wherein the delivery port opens to a side of the U-shaped strut adjacent the second leg.

21. The stent of claim 14 wherein the drug coating is further disposed on the cap end within the recess and the delivery port.

22. The stent of claim 14 wherein the cap end is uncoated.

23. The stent of claim 14 further comprising an outer drug coating disposed on at least one of the struts.

24. The stent of claim 14 wherein a first leg width of the first leg from the first fold to the drug release opening is substantially equal to a second leg width of the second leg from the single fold to the drug release opening.

25. The stent of claim 14 wherein the first leg comprises a substantially flat first leg surface from the first fold to the drug release opening, wherein the second leg comprises a substantially flat second leg surface from the first fold to the drug release opening, and wherein the substantially flat first leg surface faces the substantially flat second leg surface from the first fold to the drug release opening across the recess.

26. The stent of claim 25 wherein the recess located between the substantially flat first leg surface and the substantially flat second leg surface comprises a substantially uniform recess width between the substantially flat first leg surface and the substantially flat second leg surface from the first fold to the drug release opening.

27. A stent comprising a plurality of struts interconnected to form a tubular body, at least one of the struts comprising:
a U-shaped strut having in cross-section a first leg, a second leg, and a closed end connecting the first leg and the second leg, the first leg is longer than the second leg in cross-section, wherein the first leg, the second leg, and the closed end define a first fold, further wherein the first leg, the second leg, and the closed end define a recess extending along a long axis of the U-shaped strut, wherein the recess comprises a substantially uniform recess width having a drug coating disposed therein, the first leg having a second fold angled at about 90 degrees with respect to the first leg to form a cap end at a distal end thereof, the cap end is disposed over the recess and against the second leg to seal the drug coating within the recess, the first and second folds extending along the long axis of the U-shaped strut; and
a plurality of holes through at least one of the first leg, the second leg, the closed end and the cap end, the plurality of holes are sized to release a drug from the drug coating at a predetermined drug elution rate.

* * * * *